United States Patent [19]

Ellman et al.

[11] Patent Number: 5,630,812

[45] Date of Patent: May 20, 1997

[54] ELECTROSURGICAL HANDPIECE WITH LOCKING NOSE PIECE

[76] Inventors: Alan G. Ellman; Jon C. Garito, both of 1135 Railroad Ave., Hewlett, N.Y. 11557

[21] Appl. No.: 570,714

[22] Filed: Dec. 11, 1995

[51] Int. Cl.⁶ .................................. A61B 17/39
[52] U.S. Cl. .................. 606/41; 606/1; 606/45; 606/49
[58] Field of Search .............. 606/37–42, 45–52, 606/14–16, 1

[56] References Cited

U.S. PATENT DOCUMENTS

| | | | |
|---|---|---|---|
| 3,870,047 | 3/1975 | Gonser | 606/45 |
| 4,711,239 | 12/1987 | Sorochenko et al. | 606/48 |
| 4,754,754 | 7/1988 | Garito et al. | 606/45 |
| 5,125,058 | 6/1992 | Tenerz et al. | 606/15 |
| 5,196,007 | 3/1993 | Ellman et al. | |
| 5,267,998 | 12/1993 | Hagen | 606/49 |
| 5,456,683 | 10/1995 | Fritzsch et al. | 606/50 |

*Primary Examiner*—Angela D. Sykes
*Assistant Examiner*—Michael Peffley

[57] ABSTRACT

An electrosurgical handpiece comprises a handle and a nose piece for threaded engagement with the handle, together with a collet member which cooperates with the handle and nose piece for removably receiving and locking an electrosurgical electrode to the handle. The mating handle and nose piece are provided with locking structure adjacent their threaded portions which will automatically lock the nose piece to the handle when assembled and thus prevent the nose piece from detaching from the handle while still allowing the nose piece when the electrosurgical handpiece is in use to rotate sufficiently to cause the collet to lock and unlock to an electrode.

16 Claims, 2 Drawing Sheets

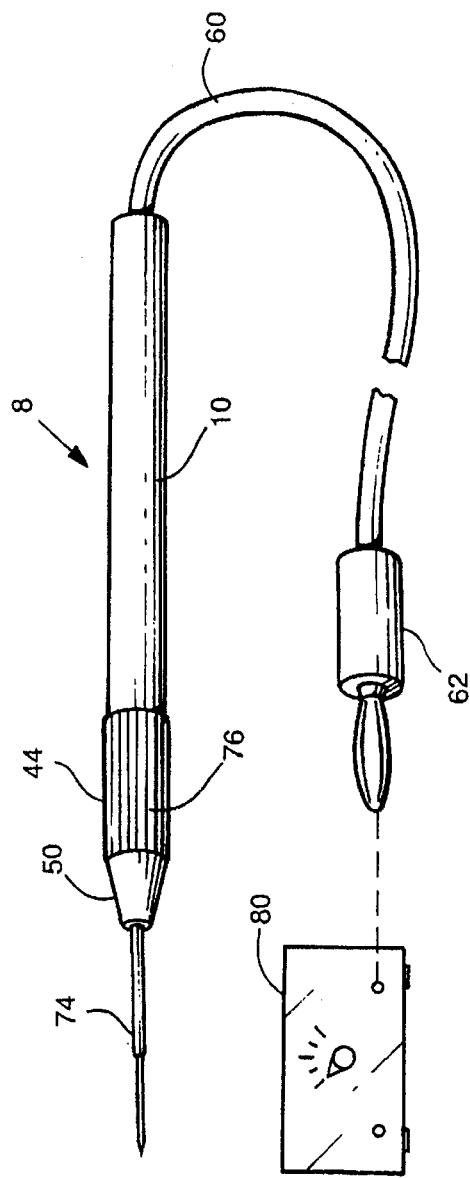
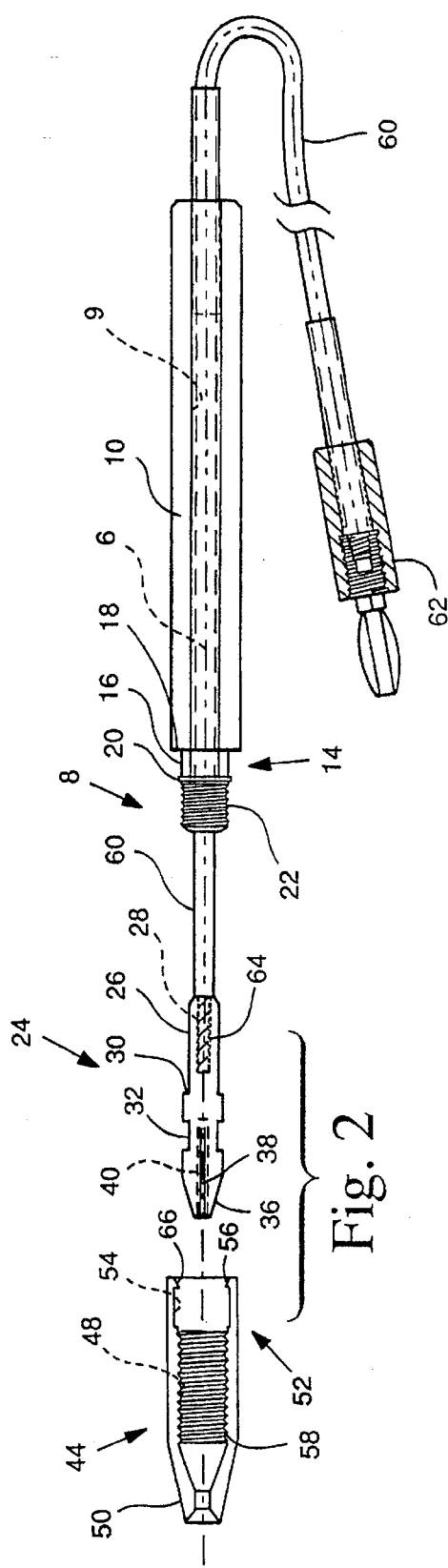

ELECTROSURGICAL HANDPIECE WITH LOCKING NOSE PIECE

This invention relates to a novel electrosurgical handpiece for receiving an electrosurgical electrode for use in electrosurgical medical, dental, and veterinarian procedures.

BACKGROUND OF THE INVENTION

Electrosurgery is a common procedure for dentists, doctors, and veternarians. Electrosurgical unipolar handpieces are commercially available that will accommodate a wide variety of electrodes shapes and sizes, such as needles, blades, scalpels, balls and wire loops. The conventional unipolar handpiece, such as that available from Ellman International, Inc. of Hewlett, N.Y. comprises an elongated electrically-insulating handle with a central bore and having at a first end an externally threaded part for threadingly engaging an internal thread on an electrically-insulating nose piece also fitted with a central bore. A generally cylindrical metal collet seats in the handle bore at the first end and a collet front portion projects forward from the handle. The collet comprises at its front portion flexible jaws formed by a tapered slitted front with a bore sized to receive the shaft or shank of a conventional electrosurgical electrode, and the nose piece has on its interior a matching tapered portion configured such that, when the nose piece is rotated clockwise (CW) while threadingly engaged to the handle, its tapered interior surface engages and gradually closes down the collet jaws so that the electrode, when inserted into the collet bore, is tightly held by the metal collet and a good electrical connection is made to the collet. The back end of the collet is connected to a wire which connects to a conventional electrosurgical instrument supplying electrosurgical currents which, when activated, via a switch on the handpiece or a foot switch or a switch on the instrument, supplies electrosurgical currents to the collet and via the collet to the electrosurgical electrode. When the dentist or doctor desires to change the shape, size or length of the electrode, it is necessary to loosen the nose piece to unlock the collet, remove the existing electrode, and substitute a new electrode.

This known handpiece, at times, can cause problems, mainly associated with the nose piece if the users are not careful. In the conventional handpiece, the nose piece is easily removable from the handle by rotating the nose piece counterclockwise (CCW). Removability, as such, may not be necessary in many situations. What is necessary, however, is that the nose piece is rotatable so that when rotated in one direction it will lock an electrode to the handpiece, and when rotated in the opposite direction it will unlock the electrode so that the electrode can be removed and replaced with another electrode. Many electrosurgical procedures require the use of several electrodes, so a handpiece is needed that will allow rapid changes of electrodes with minimum effort. The Ellman handpiece is noted for this quality. But, the ease of replacing electrodes has introduced the problem that the surgeon or assistant may not always ensure that the nose piece is properly on and properly tightened to the handle, with the result that on occasion the nose piece will detach from the handle. In most cases, this is not a serious problem, but in some case, if the nose piece detaches while the handpiece is in a patient cavity, harm could result. For example, if the cavity happens to be the mouth of the patient, the nose piece if accidentally detached may be swallowed. Another disadvantage is that if the nose piece detaches, then it or the collet may be misplaced and be unavailable when needed.

SUMMARY OF THE INVENTION

An object of the invention is an electrosurgical handpiece that can accept various shapes and sizes of electrodes by the simple expedient of rotating a nose piece, and that is capable of locking the nose piece to the handle while still allowing the nose piece to rotate sufficiently to lock and unlock the shaft of a conventional electrosurgical electrode to the handpiece.

Another object of the invention is an electrosurgical handpiece comprising separable parts including a handle, collet, and nose piece, wherein the separable parts, when assembled, are automatically locked together.

According to one aspect of the invention, an electrosurgical handpiece comprises a handle and a nose piece for threaded engagement with the handle, together with a collet member which cooperates with the handle and nose piece for removably receiving and locking an electrosurgical electrode to the handle. The mating handle and nose piece are provided with locking structure adjacent their threaded portions which will prevent the nose piece from detaching from the handle while still allowing it to rotate sufficiently to cause the collet to lock and unlock to an electrode.

In a preferred embodiment, the locking structure comprises on one of the mating members a first ridge behind its threaded portion and behind the first ridge a channeled region for receiving a second ridge on the the other of the mating members and located behind its threaded portion.

In a further preferred embodiment according to the invention, each of the mating members are provided with a ridge and an adjacent channeled region, with the ridge and adjacent channeled region on both of the mating members being located behind their respective threaded portion. For one of the mating members, the channeled region is located behind the ridge, whereas for the other of the mating members, the channeled region is located in front of the ridge.

As used herein, terms that define position are being related to the handpiece handle which possesses a longitudinal axis, and "front" means in a direction toward the electrode end of the handpiece whereas "behind " or to the "rear" means in a direction away from the electrode end of the handpiece.

Since the novel electrosurgical handpiece construction allows the use of a conventional collet, all standard electrodes can be employed to which can be attached the shaft of an electrosurgical handpiece and which can thus removably receive any one of a family of electrodes capable of performing an electrosurgical function.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention.

BRIEF DESCRIPTION OF THE DRAWINGS

In the drawings:

FIG. 1 is a perspective view of one form of an electrosurgical handpiece according to the invention shown with an electrode and shown schematically connected to an electrosurgical instrument for supply of electrosurgical currents;

FIG. 2 is an exploded view of the electrosurgical handpiece shown in FIG. 1;

Figure 3:
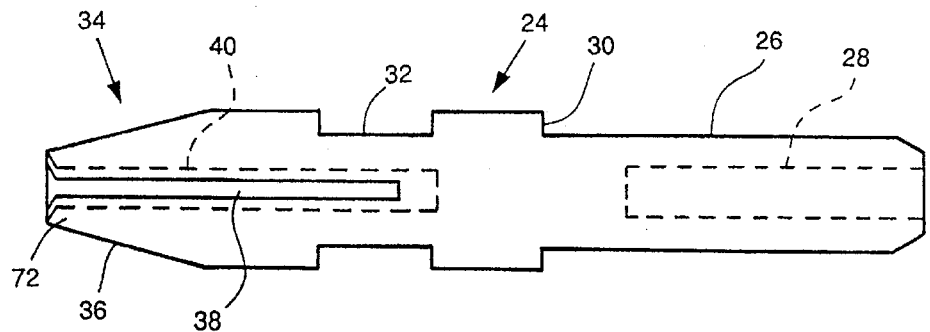
FIG. 3 illustrates one form of a collet used in the electrosurgical handpiece of the invention.

The figures are not to the same scale.

DETAILED DESCRIPTION OF THE PREFERRED EMBODIMENTS

FIGS. 1 and 2 show a preferred embodiment of an electrosurgical handpiece of the invention. The handpiece 8 comprises a straight, elongated, round handle 10 made, for example, of Delrin plastic, and provided with a bore 9 that extends throughout its length. A longitudinal axis is indicated by 6. At its left or front end is a reduced diameter cylindrical section that forms a first channeled region 14 with a cylindrical floor 16 and defined by a flanking shoulder 18 on the right and a flanking first ridge 20 on the left. The first ridge 20 is adjacent a forwardly projecting threaded portion 22.

A metal or otherwise electrically-conductive collet 24 has a rear cylindrical section 26 with a bore 28, located behind a shoulder 30, in turn behind a reduced diameter section 32 behind a standard collet head 34. The collet head 34 comprises at its left end jaws formed by a tapered part 36 that has 4 slots 38 extending radially from the outside to a bore 40.

A nose piece is shown at 44, and comprises an electrically-insulating cylindrical member, for example, of Delrin, having a central bore 48. At its left, the nose piece 44 tapers down toward its bore to form a snout 50. At its right end, inside of the bore is located a second channeled region 52 with a cylindrical floor 54 flanked at its rear by a second ridge 56. Between the second channeled region 52 and the tapered front 50 is an internally threaded portion 58, matched to the threaded portion 22 on the handle.

Figure 4:
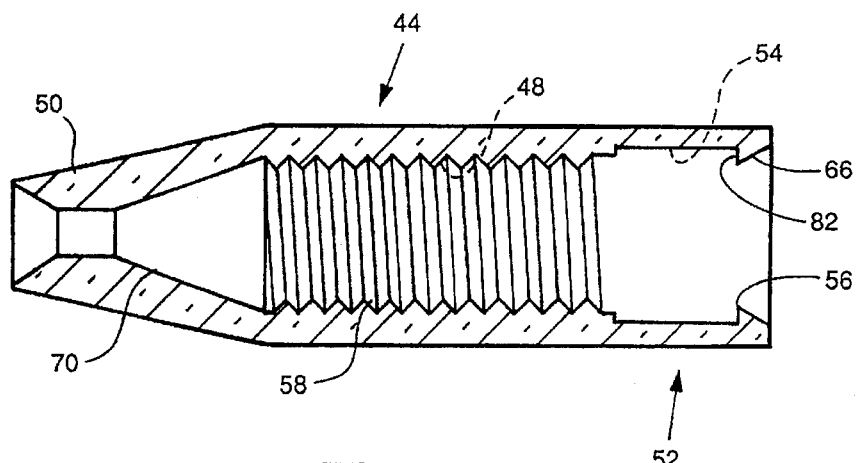
FIG. 4 illustrates one form of a nose piece used in the electrosurgical handpiece of the invention.
Figure 5:
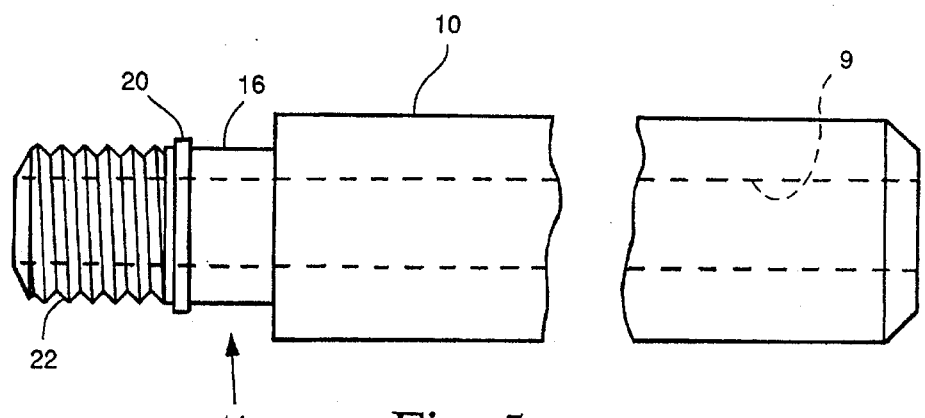
FIG. 5 illustrates one form of a handle used in the electrosurgical handpiece of the invention.

The three parts 10, 24, and 44 making up the handpiece 8 are also shown in enlarged views in FIGS. 3–5.

During the assembly process, an electrical cable 60 whose distal end is fitted with a banana plug 62 is threaded through the handle bore 9 and its free wire end soldered into the bore 28 at the rear of the collet 24, shown at 64. The cable with attached collet is then pulled to the right until stopped by the shoulder 30 with the collet rear portion 26 seating in the bore 9 within the threaded portion 22. Then, the nose piece 44 is fitted over the tapered collet end 34 and over the threaded portion 22 until the latter is engaged by the threaded portion 58 on the nose piece, and the nose piece 44 is then rotated CW to threadingly engage the mating threaded portions 22, 58. After about 8–10 turns, the second ridge 56 at the rear of the nose piece engages the first ridge 20 on the handle front end. At that point, the nose piece, with ordinary force, cannot be rotated any further.

In accordance with the invention, the ridge 56 has a bevelled rear end 66, and is configured and sized relative to the size of the ridge 20 that a much stronger force will force the second ridge 56 over the first ridge 20 and into the first channeled region 14. Simultaneously, the first ridge 20 will then be located in the second channeled region 52. Both channeled regions 14, 52 are configured and sized such that there is clearance between the innermost ridge surface and the respective channeled region floor in which it is now positioned so that the nose piece rotates freely. The length of each channeled region 14, 52, in the axial direction is such that the nose piece 44 can then be rotated at least an additional 6–10 turns such that, before it has reached the end of its travel, an interior tapered section 70 will engage the tapered front 36 of the collet 24 thereby forcing inward the collet jaws 72 defined by the slits 38. An electrode 74 whose shaft is inserted in the bore 40 of the collet will then be tightly held by the collet jaws 72 which will prevent further rotation of the nose piece 44. In the assembled condition, the electrically-insulating nose piece 44 covers the metal collet 24 except for the working end of the electrode 74 which projects forwardly from the front end of the handpiece. To ease rotation of the nose piece 44, the surface may be knurled as shown at 76.

When the plug 62 is plugged into a conventional electrosurgical instrument 80 and the instrument activated, electrosurgical currents will flow from the instrument via the cable 60 to the handpiece 8, and via the collet 24 to the electrode 74.

When it is desired to remove or replace the electrode, the nose piece 44 is rotated CCW. Sufficient rotation of the nose piece 44 is allowed by the axial length of the channeled regions to allow the natural resilience of the metal of the collet jaws 72 to relax to release the electrode which can then be withdrawn from the handpiece. However, further CCW rotation of the nose piece 44 which would allow it to be detached from the handle is prevented by the non-bevelled side 82 of the second ridge 56 which engages the rear side of the first ridge 20. Thus, the nose piece has sufficient room to rotate enough turns to allow an electrode to be tightly or loosely held and removable from the handpiece, but the nose piece cannot be detached from the handpiece because of the interfering ridges 20, 56. A feature of the invention is that for the nose piece to be able to compress the collet jaws to hold an electrode, the respective first and second ridges must be located in their respective second and first channeled regions. In other words, in order for the handpiece to operate as intended, the nose piece will always be in its locked state. Put still another way, the nose piece is automatically locked to the handle with the collet in place when the handpiece is assembled at the factory and before it reaches the user.

Successful operation depends on a suitable relationship of the size of the ridges and their adjoining channeled regions. For a conventional sized handpiece, whose length from the snout 50 in front to the rear of the handle where the cable emerges is about 5 inches(assembled), the first channeled region 14 has an axial length of about 0.1–0.3, preferably about 0.157, inches; the height of the first ridge 20 is about 0.02–0.04, preferably about 0.03, inches; and the length of the threaded portion 22 about 0.2–0.4, preferably about 0.3, inches; the second channeled region 52 has an axial length of about 0.15–0.5, preferably about 0.25, inches; the height of the second ridge 56 is about 0.04–0.07, preferably about 0.057, inches; and the length of the threaded portion 58 about 0.5–0.8, preferably about 0.69, inches. The preferred dimensions are for 5/16–24 threads. For a coarser thread pitch, the channeled regions would need to be longer, and for a finer thread, the channeled regions could be shorter. The interference between the two ridges is about 0.005 inches. This is sufficient to allow one to ride over the other when sufficient torque is applied during assembly, yet prevent their detachment during normal use. In the preferred example given, the axial length of the first channeled region 14, being shorter than that of the second channeled region 52, governs the number of turns possible of the nose piece 44.

What is not shown in the drawings are the standard switches that can be added to the handpiece so that the electrode can be turned on and off by the surgeon using the handpiece switches. Also not shown is the standard footswitch which also plugs into the electrosurgical instrument 80 for operating the handpiece.

The bore 40 of the collet 24 is sized to receive the metal shank (not shown) of an electrosurgical electrode 74. Conventional electrodes frequently come in different-sized shanks, for example, 1/16", 3/32", or 1/8". To accommodate the different sized electrodes, the handpiece when assembled can be fitted with the sized collet desired. Thus, a separate handpiece will be required for each different size of electrode shank. Typically, the collet outer dimensions are unchanged, only its bore size. In this way, each handpiece is custom sized for each type of electrode. In all cases, an electrical connection is established between the electrode conductive portions and the cable 60. The particular electrode 74 shown in FIG. 1 has an active or working end in the form of a needle. Other shapes are of course possible, such as wire loops and balls.

While the parts of the electrosurgical handpiece, made up of metal and Delrin, are auto-clavable, the device is sufficiently simple that it can be manufactured at very low cost with a less expensive plastic and thus can be made disposable.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical handpiece comprising:

an elongated handle member having a longitudinal axis and having at a first end a first threaded portion for receiving a nose piece, first means for removably receiving and holding an electrode, said first means being positioned on the handle member at its first end such that when an electrode is mounted on and gripped by the first means it projects generally parallel to the longitudinal axis in a direction frontward of the handle member, an electrode connector connected to the first means, a nose piece having a second threaded portion for threaded engagement with the first threaded portion and configured such that, when rotated while in threaded engagement with the first threaded portion of the handle member, the nose piece functions to cause the first means to tighten and to loosen its grip on the electrode, second means on the nose piece and handle member and functioning to automatically lock the nose piece to the handle member when the two are in threaded engagement yet still allow a limited amount of rotation of the nose piece relative to the handle member so it can carry out its function of causing the first means to tighten and to loosen its grip on the electrode.

2. An electrosurgical handpiece as claimed in claim 1, wherein the first means comprises a collet having jaws.

3. An electrosurgical handpiece as claimed in claim 2, wherein the nose piece has a tapered portion for engaging the collet jaws to close and open them when rotated.

4. An electrosurgical handpiece as claimed in claim 1, wherein the second means comprises a ridge on one of the nose piece and handle member and a channeled region on the other of the nose piece and handle member for engagement with the ridge.

5. An electrosurgical handpiece as claimed in claim 4, wherein the second means further comprises a ridge on the other of the nose piece and handle member and a channeled region on the one of the nose piece and handle member.

6. An electrosurgical handpiece as claimed in claim 4, wherein the channeled region has a length in the axial direction and is engageable by the ridge and determines by its length the number of turns that the nose piece can make.

7. An electrosurgical handpiece as claimed in claim 1, wherein the second means comprises a first ridge and a first channeled region on one of the nose piece and handle member and a second ridge and second channeled region on the other of the nose piece and handle member, said first and second ridges being sized to interfere yet allow one to ride over the other upon the application of excessive torque.

8. An electrosurgical handpiece as claimed in claim 7, wherein the first ridge is adjacent and to the rear of the first threaded portion and the first channeled region is adjacent and to the rear of the first ridge.

9. An electrosurgical handpiece as claimed in claim 8, wherein the second channeled region is adjacent and to the rear of the second threaded portion and the second ridge is adjacent and to the rear of the second channeled region.

10. An electrosurgical handpiece comprising:

an elongated handle member having a longitudinal axis and having at a first end a first threaded portion for receiving a nose piece, a collet for removably receiving and holding an electrode, said collet being positioned on the handle member at its first end such that when an electrode is mounted on and gripped by the collet it projects generally parallel to the longitudinal axis in a direction frontward of the handle member, an electrode connector connected to the collet, a nose piece having a second threaded portion for threaded engagement with the first threaded portion and configured such that, when rotated while in threaded engagement with the first threaded portion of the handle member, the nose piece functions to cause the collet to tighten and to loosen its grip on the electrode, means on the nose piece and handle member and functioning to automatically lock the nose piece to the handle member, in a position overlying the collet, when the nose piece and handle member are in threaded engagement yet still allow a limited amount of rotation of the nose piece relative to the handle member so it can carry out its function of causing the collet to tighten and to loosen its grip on the electrode, said means comprising a first ridge on the handle member interfering with a second ridge on the nose piece and allowing the second ridge to ride over the first ridge only upon the application of excessive turning force applied to the nose piece relative to the handle member.

11. An electrosurgical handpiece as claimed in claim 10, wherein the handle member comprises a first channeled region adjacent and to the rear of the first ridge for receiving with clearance the second ridge when it rides over the first ridge.

12. An electrosurgical handpiece as claimed in claim 11, wherein the nose piece comprises a second channeled region adjacent and in front of the second ridge for receiving with clearance the first ridge when it rides over the second ridge.

13. An electrosurgical handpiece as claimed in claim 12, wherein the first ridge is adjacent and to the rear of the first threaded portion and the first channeled region is adjacent and to the rear of the first ridge.

14. An electrosurgical handpiece as claimed in claim 13, wherein the second channeled region is adjacent and to the rear of the second threaded portion and the second ridge is adjacent and to the rear of the second channeled region.

15. An electrosurgical handpiece as claimed in claim 13, wherein the electrical connector comprises a cable electrically connected to the collet and extending through the handle member.

16. An electrosurgical handpiece as claimed in claim 15, wherein the cable is terminated in a connector.

* * * * *